United States Patent
Bonrath et al.

(10) Patent No.: US 7,321,053 B2
(45) Date of Patent: Jan. 22, 2008

(54) PROCESS FOR THE MANUFACTURE OF TOCYL AND TOCOPHERYL ACYLATES

(75) Inventors: Werner Bonrath, Freiburg (DE); Lisa Giraudi, Huningue (FR)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/554,885

(22) PCT Filed: Apr. 27, 2004

(86) PCT No.: PCT/EP2004/004443

§ 371 (c)(1),
(2), (4) Date: Oct. 28, 2005

(87) PCT Pub. No.: WO2004/096791

PCT Pub. Date: Nov. 11, 2004

(65) Prior Publication Data

US 2006/0293529 A1 Dec. 28, 2006

(30) Foreign Application Priority Data

May 2, 2003 (EP) .................................. 03009985

(51) Int. Cl.
C07C 67/02 (2006.01)
(52) U.S. Cl. ....................... 560/255; 560/254
(58) Field of Classification Search ................ 560/254, 560/255, 256, 259, 260
See application file for complete search history.

(56) References Cited

U.S. PATENT DOCUMENTS

| | | |
|---|---|---|
| 3,459,773 A | 8/1969 | Moroe et al. |
| 5,354,831 A * | 10/1994 | Panster et al. .................. 528/9 |
| 5,703,272 A | 12/1997 | Abe et al. |
| 5,922,900 A | 7/1999 | Wieland et al. |
| 6,784,303 B2 * | 8/2004 | Oost et al. .................. 549/408 |

FOREIGN PATENT DOCUMENTS

| | | | |
|---|---|---|---|
| EP | 0 582 811 A1 | | 2/1994 |
| EP | 0 997 193 A1 | | 5/2000 |
| JP | 49 055633 A | | 5/1974 |
| JP | 49055633 | * | 5/1974 |
| WO | WO98/25876 | | 6/1998 |
| WO | WO 02/42286 A1 | | 5/2002 |
| WO | 2004096790 | * | 11/2004 |

OTHER PUBLICATIONS

Derwent Database English language abstract of WO 02/42286 (B1 above), WPI Accession No. 2002-479948/200251.
Derwent Database English language abstract of EP 0 582 811 (B2 above), WPI Accession No. 1993-369887/199347.
Derwent Database English language abstract of EP 0 997 193 A1 (B3 above), WPI Accession No. 2000-293944/200026.
Derwent Database English language abstract of JP 49 055633 A (B5 above), Abstract No. XP002292233.

* cited by examiner

Primary Examiner—Karl Puttlitz
(74) Attorney, Agent, or Firm—Bryan Cave LLP

(57) ABSTRACT

A process for the manufacture of a tocyl acylate or a tocopheryl acylate comprises reacting tocol or a tocopherol with an acylating agent in the presence of a solid heterogeneous Brönsted acid catalyst, said catalyst being an inorganic Brönsted acid on a solid carrier material which comprises silicon dioxide, titanium dioxide or both silicon dioxide and titanium dioxide, or being an organofunctional polysilonaxe featuring sulpho groups, the solid heterogeneous Brönsted acid catalyst further featuring a BET surface area from about 10 $m^2/g$ to about 800 $m^2/g$ and a pore volume from about 0.1 ml/g to about 2.0 ml/g. The main commercial form of vitamin E, being (all-rac)-α-tocopheryl acetate, can be manufactured by acylation of (all-rac)-α-tocopherol according to this process.

15 Claims, No Drawings

PROCESS FOR THE MANUFACTURE OF TOCYL AND TOCOPHERYL ACYLATES

The present invention is concerned with a novel process for the manufacture of acylates of tocol and of tocopherol.

The term "tocopherol" as used herein is to be understood to refer to any compound derived from the basic structure of tocol [2-methyl-2-(4,8,12-trimethyltridecyl)-6-chromanol] and having vitamin E character, viz. any tocopherol having the saturated side chain 4,8,12-trimethyltridecyl, such as α-, β-, γ-, δ-, ζ$_2$- or η-tocopherol, and also any tocotrienol having three double bonds in the side chain [4,8,12-trimethyltridec-3,7,11-trienyl], such as ε- or ζ$_1$-tocopherol. Of generally referred to as vitamin E, is of primary interest, being the most active and industrially most important member of the vitamin E group.

The present invention is preferably concerned with a novel process for the manufacture of acylates of tocopherols (tocopheryl acylates), more particularly tocopheryl acetates. The main commercial form of vitamin E being (all-rac)-α-tocopheryl acetate, the invention, in a more preferred aspect, is concerned with a process for the manufacture of (all-rac)-α-tocopheryl acetate. However, tocol itself and the other tocopherols such as those mentioned above can be readily acylated by the process of the present invention. In general, tocol and each of the tocopherols can be acylated in the form of an all-racemic mixture of its diastereoisomers (diasereoisomeric pairs of enantiomers) or of any individual stereoisomer.

The synthesis of α-tocopheryl acetate by esterification of α-tocopherol with excess acetic anhydride in the absence of a catalyst is described and exemplified by J. D. Surmatis et al. in U.S. Pat. No. 2,723,278. The product, "dl-α-tocopheryl acetate", was formed under reflux conditions for 3 or 5 hours; the yield is not given. This reaction can also be carried out with pyridine as the catalyst to afford, after three days reaction at room temperature, α-tocopheryl acetate in 96% yield, as reported by N. Cohen et al. on page 1172 of Helv. Chim. Acta. 64, 1158-1172 (1981).

The novel process according to the present invention provides excellent yields, avoids corrosion problems and can be carried in the absence of an additional solvent, thus avoiding the need to recycle solvents, and can be carried out in a continuous or batchwise mode.

According to the present invention there is provided a process for the manufacture of an acylate of tocol or a tocopherol (tocyl acylate or a tocopheryl acylate) which comprises reacting tocol or a tocopherol with an acylating agent in the presence of a solid heterogeneous Brönsted acid catalyst, said catalyst being an inorganic Brönsted (protonic) acid on a solid carrier material which comprises silicon dioxide, titanium dioxide or both silicon dioxide and titanium dioxide, or being an organofunctional polysiloxane featuring sulpho (—SO$_3$H) groups, the solid heterogeneous Brönsted acid catalyst further featuring a BET surface area from about 10 m$^2$/g to about 800 m$^2$/g and a pore volume from about 0.1 ml/g to about 2.0 ml/g.

The inorganic Brönsted acid is suitably sulphuric acid or orthophosphoric acid (also commonly known as phosphoric acid; H$_3$PO$_4$), and such an acid is carried or supported on the solid carrier material, which itself comprises silicon dioxide, titanium dioxide or both silicon dioxide and titanium dioxide, particularly by adsorption thereon, the whole constituting the solid heterogeneous Brönsted acid catalyst. Such solid heterogeneous Brönsted acid catalysts are known from and/or can be produced by the skilled artisan by following the teachings in inter alia the European Patent Publications Nos. 0 452 619 B1, 0 807 615 B1, 0 916 402 A1 and 0 997 193 A1 and the further references cited therein. In some of these references phosphoric acid is mentioned as a Brönsted acid which may be carried or supported on the solid carrier material, and this applies analogously also for sulphuric acid as the carried or supported Brönsted acid. The solid carrier material may if desired contain in addition to silicon dioxide and/or titanium dioxide further metal oxide such as zinc oxide, but such an additional metal oxide is generally present to a much lesser extent than the silicon dioxide and/or the titanium dioxide, preferably constituting up to about 5 weight percent (wt. %) of the total mixed metal oxide carrier. Where silicon dioxide (SiO$_2$) and titanium dioxide (TiO$_2$) are both present in the carrier material, the relative weight ratio SiO$_2$:TiO$_2$ is suitably from about 80:20 to about 95:5. Moreover, the amount of carried/supported Brönsted acid is suitably from about 0.01 to about 70 wt. %, preferably from about 0.1 to about 20 wt. %, and most preferably from about 1 to about 5 wt. %, relative to the weight of the solid heterogeneous Brönsted acid catalyst as a whole (acid and solid carrier material together). Examples of the solid carrier material are the various grades of formed pyrogenic silica or titania commercially available under the trademark Aerolyst®, such as those with the reference numbers 3038-3046, 350 and 355 (pyrogenic silica) and 7706 and 7708-7711 (pyrogenic titania), in tablet, extrudate, ring or other form from suppliers, particularly from Degussa AG, Postfach 302043, 40402 Düsseldorf, Germany, or local outlets of this company in other countries. Examples of the solid heterogeneous Brönsted acid catalysts of this type themselves are a solid comprising about 80-95 wt. % of silicon dioxide and about 10 wt. % of titanium dioxide as the carrier material and up to about 15 wt. % (relative to the weight of the aforementioned carrier material) of sulphuric acid as the inorganic Brönsted acid; a solid comprising about 80-95 wt. % of silicon dioxide, up to about 5 wt. % of zinc oxide and up to about 15 wt. % of sulphuric acid (these weights being relative to the total weight of the carrier substances and the acid); a solid consisting practically entirely of titanium dioxide and about 1 wt. % (relative to the weight of this carrier material) of sulphuric acid; and a solid comprising about 30-70 wt. % of silicon dioxide, up to about 5 wt. % of titanium dioxide and about 30-70 wt. % of orthophosphoric acid (these weights being relative to the total weight of the carrier substances and the acid).

As the alternative solid heterogeneous Brönsted acid catalysts, the organofunctional polysiloxanes featuring sulpho groups are polysiloxanes bearing sulphohydrocarbyl groups. In particular, they have a basic polymeric silicate structure with repeating —Si—O— units in the matrix and in which are present, chemically integrated and attached to some of the silicon atoms, acid-functional groups of the formula —R—SO$_3$H wherein R is a divalent hydrocarbyl group. Such organofunctional polysiloxanes featuring sulpho groups are producible in known manner by polycondensation of difunctional organosilicon compounds of the appropriate general formula (HO)$_3$Si—R—SO$_3$H, optionally together with tetrahydroxysilane ["orthosilicic acid", Si(OH)$_4$]. Examples of such difunctional organosilicon compounds are terminally trihydroxysilyl substituted C$_{1-12}$-alkanesulphonic acids, e.g. 3-(trihydroxysilyl)-1-propanesulphonic acid; trihydroxysilyl-C$_{5-8}$-cycloalkanesulphonic acids, (trihydroxysilyl-C$_{1-6}$-alkyl)-cyclohexanesulphonic acids, trihydroxysilyl-cyclohexyl-C$_{1-6}$-alkanesulphonic acids and (trihydroxysilyl-C$_{1-6}$-alkyl)-cyclohexyl-C$_{1-6}$-alkanesulphonic acids; and trihydroxysilyl-benzenesulphonic acid, (trihydroxysilyl-C$_{1-6}$-alkyl)- benzenesulphonic acids, trihydroxysilyl-phenyl-$C_{1-6}$-alkanesulphonic acids and (trihydroxysilyl-$C_{1-6}$-alkyl)-phenyl-$C_{1-6}$-alkanesulphonic acids, e.g. [p-(trihydroxysilylmethyl)-phenyl]methanesulphonic acid. The last-mentioned compounds featuring a benzene (phenyl) moiety may feature methyl substitution on said moiety. In such sulphonylated organosilicon compounds the $C_{1-12}$-alkane, $C_{1-6}$-alkane and $C_{1-6}$-alkyl moieties when containing 2 or more carbon atoms may in each case be straight or branched chain. The organofunctional polysiloxanes featuring sulpho groups used as the solid heterogeneous Brönsted acid catalysts in the process of the present invention are preferably polysiloxanes bearing sulphoalkyl or sulphoaryl groups (so-called acid-functional groups) of the formula —$(CH_2)_x$—$SO_3H$ or -arylene-$SO_3H$, respectively, wherein x is an integer from 1 to 3, and arylene is a divalent aromatic group derived from benzene, e.g. 1,4-phenylene, or toluene, e.g. 2-methyl-1,4-phenylene. The acid-functional groups are most preferably 3-sulphopropyl, of the formula —$(CH_2)_3$—$SO_3H$.

The polymerized matrix of the organofunctional polysiloxanes featuring sulpho groups may if desired also feature, as well as integral silicon atoms, titanium and/or aluminium atoms integrated in a like manner to the silicon atoms in the whole matrix.

Such organofunctional polysiloxane featuring sulpho groups preferably features a molar ratio of silicon atoms to sulpho groups of at least 2:1.

As indicated above, they are producible in known manner by polycondensation of difunctional organic silicon compounds of the appropriate general formula $(HO)_3Si$—R—$SO_3H$, e.g. $(HO)_3Si$—$(CH_2)_x$—$SO_3H$ or $(HO)_3Si$-arylene-$SO_3H$, optionally together with tetrahydroxysilane ["orthosilicic acid", $Si(OH)_4$]. Details on the structure and preparation of the organofunctional polysiloxanes featuring sulpho groups are to be found for example in CLB (Chemie in Labor und Biotechnik, 43. Jahrgang, Heft 1/1993, pages 16-21., the German Patent Publication (Offenlegungsschrift) No. 3226093 A1 and the European Patent Publication No. 0 582 811 B1, and the further references cited therein.

The organofunctional polysiloxanes featuring sulpho groups for use as the alternative type of solid heterogeneous Brönsted acid catalysts in the process of the present invention are also generally commercially available from suppliers, particularly from Degussa AG, Postfach 302043, 40402 Düsseldorf, Germany, or local outlets of this company in other countries. Some have been available from Degussa AG under the trademark Deloxan®, e.g. Deloxan® ASP 1/9.

The acylation can be carried out in principle using any acylating agent conventionally used for the acylation of a phenolic hydroxyl group as is present in tocol and tocopherols. Especially suitable types of such acylating agents are acid anhydrides and acyl halides. The acyl groups in such acylating agent may be derived from aliphatic carboxylic acids, e.g. from straight or branched chain alkanoic acids, in particular $C_{1-7}$-alkanoic acids such as acetic acid, propionic acid, butyric acid and pivalic acid, or from higher alkanoic acids (fatty acids) with up to 20 carbon atoms such as palmitic acid; or from aromatic carboxylic acids, particularly benzoic acid, so that in each case the appropriate acylate, being an alkanoate, or e.g. the benzoate, respectively, of tocol or the tocopherol is produced in the acylation process. Examples of aliphatic acyl halides are straight or branched chain alkanoyl chlorides such as acetyl, propionyl and butyryl chloride, and an example of aromatic acyl halides is benzoyl chloride. The preferred acylating agent is acetic anhydride or acetyl chloride, most preferably acetic anhydride.

The acylation in accordance with the present invention may by carried out in the presence or in the absence of an added solvent, but preferably one of the reactants, i.e. tocol or the tocopherol as the one reactant or the acylating agent as the other reactant, is used in excess and no added solvent used. Preferably, the acylating agent is used in excess, preferably in a one- to about a sixfold molar amount, more preferably in a 1.5- to 2.5-fold molar amount, and most preferably in a 1.75- to 2.25-fold molar amount, relative to the molar amount of tocol or the tocopherol present in the initial reaction mixture. If an additional solvent is used, however, this is suitably a polar or non-polar aprotic organic solvent, particularly an aliphatic, preferably $C_4$ to $C_{10}$ aliphatic, hydrocarbon, e.g. pentane, hexane, heptane or decane; an alicyclic, preferably $C_5$ to $C_7$ alicyclic, hydrocarbon, e.g. cyclohexane; or an aromatic, particularly $C_6$ to $C_{10}$ aromatic, hydrocarbon, e.g. benzene, toluene, an xylene or naphthalene.

The amount of the solid heterogeneous Brönsted acid catalyst used is based on the amount of the reactant, i.e. tocol or the tocopherol or the acylating agent, usually the former, which is used in the lesser molar amount and is suitably in the range from about 0.0025 to about 0.025 grammes (g) per g of the reactant used in said lesser molar amount, when the process is effected in a batchwise operational mode. For the alternative, and preferred, continuous operational mode, the relative amount of catalyst will be adjusted to the size of the reactor and the flow of the reactants. In this case it will be appreciated that the determination of the appropriate relative amount based on the figures for the batchwise operational mode is within the normal skill of the production chemist.

The acylation process in accordance with the present invention is conveniently carried out in a temperature range from about 80° C. to about 120° C., preferably from about 90° C. to about 110° C.

Moreover, the process is conveniently carried out under an inert gas atmosphere, preferably under gaseous nitrogen or argon, especially the former.

The progress of the reaction is suitably monitored by analytical means, such as gas chromatographical analysis of samples taken from the reaction mixture at various time intervals during the reaction.

After completion of the acylation the produced tocyl or tocopheryl acylate can be isolated by cooling the mixture after acylation, neutralization by addition of a suitable base, e.g. sodium carbonate, filtration of the mixture, and distilling off from the filtrate, preferably under reduced pressure, the remaining (unreacted) tocol or tocopherol or acylating agent, whichever has been used in excess, and the secondary product formed in the acylation, e.g. acetic acid when acetic anhydride is used as the acylating agent, followed by further distillation, also preferably under reduced pressure, to collect as pure a fraction of the desired acylation product as required.

The process in accordance with the present invention is illustrated by the following Examples.

EXAMPLE 1

16.8 g (38.7 mmol) of (all-rac)-α-tocopherol were dissolved in 8.23 g (80.6 mmol) of acetic anhydride in the presence of 0.5 g of Deloxan® ASP 1/9 (a solid heterogeneous Brönsted acid catalyst comprising amorphous silicon dioxide and about 20-25 wt. % relative to the whole weight of an organopolysiloxane containing sulpho groups derived from 3-(trihydroxysilyl)-1-propanesulphonic acid, and having a BET surface area in the range of about 400 to about 600 m²/g and a pore volume in the range of about 1.5 to about 2.0 ml/g) in a 50 ml four-necked flask equipped with a stirrer, a thermometer, a reflux condenser and argon gasification means. The mixture was stirred at 400 rpm and heated at 100° C. (internal temperature) for 1.5 hours. The mixture was cooled to 28° C., neutralized with 5 g of sodium carbonate, filtered, washed with 70 ml of heptane and evaporated under reduced pressure [10 mbar (1 kPA), 40° C.]. 18.45 g of a brownish oil were obtained with a purity of 97.52% tocopheryl acetate (analyzed by gas chromatography: GC) which corresponds to a yield of 98.3% based on (all-rac)-α-tocopherol. The crude product was further purified by bulb-to-bulb distillation at 207° C. [0.012 mbar (1.2 Pa)]. The pure product was isolated as a colourless-light yellowish oil in 98.0% purity (GC). There were obtained 17.52 g of (all-rac)-α-tocopheryl acetate, representing a yield of 96.8% based on (all-rac)-α-tocopherol.

EXAMPLE 2

16.8 g (38.7 mmol) of (all-rac)-α-tocopherol were dissolved in 8.23 g (80.6 mmol) of acetic anhydride in the presence of 0.5 g of a solid heterogeneous Brönsted acid catalyst comprising about 80-95 wt. % of silicon dioxide, up to about 5 wt. % of zinc oxide and up to about 15 wt. % of sulphuric acid, and having a pore volume of 0.98 ml/g, in a 50 ml four-necked flask equipped with a stirrer, a thermometer and a reflux condenser with argon gasification means. The mixture was stirred at 400 rpm and heated at 100° C. (internal temperature) for 2 hours. The mixture was then cooled to 28° C., neutralized with 5 g of sodium carbonate, filtered, washed with 70 ml of heptane and evaporated under reduced pressure [10 mbar (1 kPA), 40° C.]. 18.79 g of a brownish oil were obtained with a purity of 97.31% (all-rac)-α-tocopheryl acetate (analyzed by GC). The crude product was further purified by bulb-to-bulb distillation at 205° C. [0.013 mbar (1.3 Pa)]. The pure product was isolated as a colourless-light yellowish oil in 97% purity (GC, internal standard). There were obtained 17.71 g of (all-rac)-α-tocopheryl acetate, representing a yield of 97.8% based on (all-rac)-α-tocopherol.

EXAMPLE 3

In analogy to Example 2 but using a solid heterogeneous Brönsted acid catalyst comprising amorphous silicon dioxide and about 20-25 wt. % relative to the whole weight of an organopolysiloxane containing sulpho groups derived from 3-(trihydroxysilyl)-1-propanesulphonic acid, and having a BET surface area of 100 m²/g and a pore volume of 1.3 ml/g, (all-rac)-α-tocopheryl acetate was obtained in a yield, after bulb-to-bulb distillation of the crude product, of 97.4% based on (all-rac)-α-tocopherol.

EXAMPLE 4

In analogy to Example 2 but using a solid heterogeneous Brönsted acid catalyst comprising about 80-95 wt. % of silicon dioxide and about 10 wt. % of titanium dioxide as the carrier material and up to about 15 wt. % (relative to the weight of the carrier material) of sulphuric acid, and having a BET surface area of 46 m²/g and a pore volume of 0.33 ml/g, (all-rac)-α-tocopheryl acetate was obtained in a yield, after bulb-to-bulb distillation of the crude product, of 98.8% based on (all-rac)-α-tocopherol.

EXAMPLE 5

In analogy to Example 2 but using a solid heterogeneous Brönsted acid catalyst consisting practically entirely of titanium dioxide and about 1 wt. % (relative to the weight of this carrier material) of sulphuric acid, and having a BET surface area of 46 m²/g and a pore volume of 0.33 ml/g, (all-rac)-α-tocopheryl acetate was obtained in a yield, after bulb-to-bulb distillation of the crude product, of 97.0% based on (all-rac)-α-tocopherol.

EXAMPLE 6

In analogy to Example 2 but using a solid heterogeneous Brönsted acid catalyst comprising about 80-95 wt. % of silicon dioxide and about 10 wt. % of titanium dioxide as the carrier material and up to about 15 wt. % (relative to the weight of the carrier material) of sulphuric acid, and having a BET surface area of 46 m²/g and a pore volume of 0.33 ml/g, (all-rac)-α-tocopheryl acetate was obtained in a yield, after bulb-to-bulb distillation of the crude product, of 97.0% based on (all-rac)-α-tocopherol.

EXAMPLE 7

In analogy to Example 2 but using a solid heterogeneous Brönsted acid catalyst comprising about 30-70 wt. % of silicon dioxide, up to about 5 wt. % of titanium dioxide and about 30-70 wt. % of orthophosphoric acid (these weights being relative to the total weight of the carrier substances and the acid) as the catalyst and after a reaction time of 12 hours (all-rac)-α-tocopheryl acetate was obtained in a yield, after bulb-to-bulb distillation of the crude product, of 96.5% based on (all-rac)-α-tocopherol.

EXAMPLE 8

17.03 g (38.7 mmol) of (all-rac)-γ-tocopherol were dissolved in 8.21 g (80.58 mmol) of acetic anhydride in the presence of 0.51 g of Deloxan® ASP 1/9 (see Example 1 for its specification) in a 50 ml four-necked flask equipped with a stirrer, a thermometer and a reflux condenser with argon gasification means. The mixture was stirred at 400 rpm and heated to 100° C. (internal temperature) for 1 hour. The mixture was cooled to 40° C. and evaporated under reduced pressure [10 mbar (1 kPA), 50° C.)]. 19.78 g of a brownish oil was obtained with a purity of 88.57% (all-rac)-γ-tocopheryl acetate, analyzed by GC (internal standard). The yield was 17.51 g, based on (all-rac)-γ-tocopherol. The crude product (19.78 g) was further purified by bulb-to-bulb distillation at 211° C. [0.015 mbar (1.5 Pa)]. The pure product was isolated as a colourless-light yellowish oil in 94.16% purity (GC, internal standard). There were obtained 17.11 g of (all-rac)-γ-tocopheryl acetate, representing a yield of 93.5% based on (all-rac)-γ-tocopherol.

EXAMPLE 9

A solution of 500 g of (all-rac)-α-tocopherol (98.99% purity, 1.149 mol) and 592 g (0.55 l, 5.8 mol) of acetic anhydride was pumped through a reactor filled with 4.75 g of Deloxan® ASP 1/9 (see Example 1 for its specification) at a feed rate 0.4 ml/minute at 100° C. for 12 days. During the reaction several samples were taken and worked up. During 2 hours a solution of 46.48 g of crude reaction product was collected. The excess acetic anhydride was distilled off and the crude product (23.83 g) was transferred to a flask and the 23.21 g therein purified by bulb-to-bulb distillation at 206° C. [0.0054 mbar (0.15 Pa)]. The material (22.67 g) with a purity of 97.5% (22.1 g) tocopheryl acetate was analyzed (GC internal standard). The residue contained 0.36 g (88.89%) of tocopheryl acetate and unknowns. In the cooling traps 0.22 g of solvent was found. The total yield of (all-rac)-α-tocopheryl acetate was 22.42 g (97.0%), after bulb-to-bulb distillation 22.1 g (95.6%).

The invention claimed is:

1. A process for the manufacture of a tocyl acylate or a tocopheryl acylate which comprises reacting tocol or a tocopherol with an acylating agent in the presence of a solid heterogeneous Brönsted acid catalyst, said catalyst being an inorganic Brönsted acid on a solid carrier material which comprises both silicon dioxide and titanium dioxide, the solid heterogeneous Brönsted acid catalyst further featuring a BET surface area from about 10 $m^2/g$ to about 800 $m^2/g$ and a pore volume from about 0.1 ml/g to about 2.0 ml/g.

2. A process according to claim 1 wherein the inorganic Brönsted acid is sulphuric acid or orthophosphoric acid.

3. A process according to claim 1, wherein silicon dioxide ($SiO_2$) and titanium dioxide ($TiO_2$) are both present in the carrier material and the relative weight ratio $SiO_2:TiO_2$ is from 80:20 to about 95:5.

4. A process according to claim 1, wherein the amount of carried/supported inorganic Brönsted acid is from about 0.01 to about 70 wt. % relative to the weight of the solid heterogeneous Brönsted acid catalyst as a whole.

5. A process according to claim 1, wherein the reaction is carried out with one of the reactants in excess and in the absence of an added solvent.

6. A process according to claim 5 wherein the acylating agent is used in excess, relative to the molar amount of tocol or the tocopherol present in the initial reaction mixture.

7. A process according to claim 1, wherein the reaction is effected in a batchwise operational mode and the amount of the solid heterogeneous Brönsted acid catalyst used based on the amount in grammes of the reactant which is used in the lesser molar amount is in the range from about 0.0025 to about 0.025 g/g.

8. A process according to claim 1, wherein the reaction is carried out at temperatures from about 80° C. to about 120° C.

9. A process according to claim 1, wherein (all-rac)-α-tocopherol is acylated to (all-rac)-α-tocopheryl acetate.

10. A process according to claim 1, wherein the reaction is carried out in a continuous operational mode.

11. A process according to claim 4, wherein the amount of carried/supported inorganic Brönsted acid is from about 0.1 to about 20 wt. % relative to the weight of the solid heterogeneous Brönsted acid catalyst as a whole.

12. A process according to claim 11, wherein the amount of carried/supported inorganic Brönsted acid is from about 0.1 to about 1 to about 5 wt. % relative to the weight of the solid heterogeneous Brönsted acid catalyst as a whole.

13. A process according to claim 6 wherein the acylating agent is used in about one-to about a sixfold molar amount relative to the molar amount of tocol or the tocopherol present in the initial reaction mixture.

14. A process according to claim 13 wherein the acylating agent is used in about 1.5- to about 2.5-fold molar amount relative to the molar amount of tocol or the tocopherol present in the initial reaction mixture.

15. A process according to claim 14 wherein the acylating agent is used in about 1.75- to about 2.25-fold molar amount relative to the molar amount of tocol or the tocopherol present in the initial reaction mixture.

* * * * *